United States Patent
Keller et al.

(10) Patent No.: US 9,023,046 B2
(45) Date of Patent: May 5, 2015

(54) IMPLANT FOR FRACTURE TREATMENT

(75) Inventors: Samuel Keller, Hettlingen (CH);
Miodrag Garic, Winterthur (CH);
Hermann Stricker, Rifferswil (CH);
Reto Senger, Winterthur (CH); Daniel Bühler, Wiesendangen (CH); Andreas E. Schwammberger, Ramlinsburg (CH);
Serene H. Longsworth, Randolph, NJ (US)

(73) Assignee: Zimmer GmbH, Winterthur (CH)

( * ) Notice: Subject to any disclaimer, the term of this patent is extended or adjusted under 35 U.S.C. 154(b) by 866 days.

(21) Appl. No.: 12/531,557

(22) PCT Filed: Feb. 25, 2008

(86) PCT No.: PCT/EP2008/052254
§ 371 (c)(1),
(2), (4) Date: Dec. 9, 2009

(87) PCT Pub. No.: WO2008/102016
PCT Pub. Date: Aug. 25, 2008

(65) Prior Publication Data
US 2010/0179549 A1    Jul. 15, 2010

(30) Foreign Application Priority Data
Feb. 23, 2007    (CH) ........................ 309/07

(51) Int. Cl.
*A61B 17/56*    (2006.01)
*A61B 17/74*    (2006.01)
*A61B 17/72*    (2006.01)
*A61B 17/86*    (2006.01)

(52) U.S. Cl.
CPC ............ *A61B 17/746* (2013.01); *A61B 17/744* (2013.01); *A61B 17/7241* (2013.01); *A61B 17/866* (2013.01); *A61B 17/8685* (2013.01); *A61B 2017/8655* (2013.01)

(58) Field of Classification Search
CPC ................................... A61B 17/7241
USPC ..................................... 606/62–68
See application file for complete search history.

(56) References Cited

U.S. PATENT DOCUMENTS 2,381,050 A * 8/1945 Hardinge ..................... 606/65
2,607,259 A   8/1952 Forster
(Continued)

FOREIGN PATENT DOCUMENTS

WO    WO2007/016796 A1    2/2007
WO    WO2009/023182 A1    2/2009

OTHER PUBLICATIONS

HeliCoil Insert Systems, Emhart Teknologies, 2008 HC2000 Rev 4.
(Continued)

*Primary Examiner* — Kevin T Truong
*Assistant Examiner* — Stuart S Bray
(74) *Attorney, Agent, or Firm* — Schwegman Lundberg & Woessner, P.A.

(57) ABSTRACT

An implant is described for fracture treatment, comprising an elongate and in particular substantially rotationally symmetrical base body (20), in particular an implant shaft, and an anchoring section (10), wherein the anchorage section has an outer surface of a porous biocompatible material at least in part, and wherein the anchorage section is arranged in an axial end region of the implant and is releasably connectable to the base body.

11 Claims, 8 Drawing Sheets

(56) References Cited

U.S. PATENT DOCUMENTS

| | | | |
|---|---|---|---|
| 2,934,123 | A | 4/1960 | Brancato |
| 3,193,858 | A | 7/1965 | Kahn |
| 3,840,904 | A | 10/1974 | Tronzo |
| 3,945,070 | A | 3/1976 | Hauser |
| 4,077,101 | A | 3/1978 | Wallace |
| 4,601,092 | A | 7/1986 | Guitaut et al. |
| 5,108,446 | A | 4/1992 | Wagner et al. |
| 5,152,948 | A | 10/1992 | Lizenby |
| 5,211,665 | A | 5/1993 | Ku |
| 5,282,861 | A | 2/1994 | Kaplan |
| 5,360,452 | A | 11/1994 | Engelhardt et al. |
| 5,366,328 | A | 11/1994 | Helderman |
| 5,507,827 | A | 4/1996 | Grundei et al. |
| 5,769,897 | A | 6/1998 | Harle |
| 6,228,121 | B1 | 5/2001 | Khalili |
| 7,597,715 | B2 * | 10/2009 | Brown et al. ............... 623/22.32 |
| 7,918,382 | B2 * | 4/2011 | Charlebois et al. ........ 228/248.1 |
| 8,047,735 | B2 * | 11/2011 | Broadley et al. .............. 401/265 |
| 8,109,932 | B2 * | 2/2012 | Lytinas ....................... 606/86 R |
| 8,197,499 | B2 * | 6/2012 | Gurtner et al. ................ 606/153 |
| 8,216,259 | B2 * | 7/2012 | Gurtner et al. ................ 606/153 |
| 2002/0161369 | A1 | 10/2002 | Bramlet et al. |
| 2003/0045885 | A1 | 3/2003 | Margulies et al. |
| 2003/0083662 | A1 | 5/2003 | Middleton |
| 2004/0093090 | A1 * | 5/2004 | Barbieri et al. ............... 623/22.3 |
| 2005/0184134 | A1 * | 8/2005 | Charlebois et al. ........ 228/248.1 |
| 2006/0142763 | A1 * | 6/2006 | Munro et al. ..................... 606/62 |
| 2006/0241776 | A1 * | 10/2006 | Brown et al. ................ 623/20.16 |
| 2007/0010814 | A1 * | 1/2007 | Stauch ............................ 606/62 |
| 2007/0162011 | A1 * | 7/2007 | Leyden et al. .................. 606/65 |
| 2007/0173838 | A1 * | 7/2007 | Li ..................................... 606/67 |
| 2007/0173948 | A1 * | 7/2007 | Meridew et al. ........... 623/22.24 |
| 2007/0244485 | A1 * | 10/2007 | Greenhalgh et al. ............ 606/86 |
| 2007/0270848 | A1 * | 11/2007 | Lin .................................. 606/65 |
| 2008/0021453 | A1 * | 1/2008 | Dutoit et al. ..................... 606/61 |
| 2008/0046091 | A1 * | 2/2008 | Weiss et al. ................. 623/22.37 |
| 2008/0091205 | A1 * | 4/2008 | Kuiper et al. .................... 606/64 |
| 2008/0119854 | A1 * | 5/2008 | Johnstone ........................ 606/64 |
| 2008/0195098 | A1 * | 8/2008 | Gotfried ........................... 606/62 |
| 2008/0195222 | A1 * | 8/2008 | Rauguth et al. .............. 623/23.6 |
| 2008/0255558 | A1 * | 10/2008 | Schlienger et al. ............. 606/62 |
| 2008/0269745 | A1 * | 10/2008 | Justin .............................. 606/62 |
| 2008/0294163 | A1 * | 11/2008 | Chou et al. ...................... 606/62 |
| 2008/0294164 | A1 * | 11/2008 | Frank et al. ..................... 606/64 |
| 2009/0088807 | A1 | 4/2009 | Castaneda |
| 2009/0192610 | A1 | 7/2009 | Case et al. |
| 2010/0179549 | A1 * | 7/2010 | Keller et al. .................... 606/62 |
| 2011/0004212 | A1 * | 1/2011 | Gall et al. ....................... 606/62 |
| 2011/0208189 | A1 * | 8/2011 | Faccioli et al. ................. 606/62 |

OTHER PUBLICATIONS

High-Porosity Titanium, Stainless Steel, and Superalloy Parts; Martin Bram, Cornelia Stiller, Hans Peter Buchkremer, Detlev Stover and Hartmut Baur; Advanced Engineering Materials 2000, 2, No. 4; pp. 196-199.

Partial Search Report mailed Nov. 9, 2010 in related International Application No. PCT/US2010/040415.

Spiralock, Wire Thread Insert Installation Instructions, 3 pages, date unknown.

Zimmer NexGen Trabecular Metal Augments, Surgical Technique for LCCK & Rotating Hing Knee Trabecular Metal Augments, 2004 Zimmer, Inc. 97-5448-02 Rev. 1.

International Search Report from PCT/EP2008/052254 published Aug. 28, 2008.

English translation of the International Preliminary Report on Patentability.

"International Application Serial No. PCT/EP2008/052254, International Preliminary Report on Patentability mailed Apr. 14, 2009", 9 pgs.

"International Application Serial No. PCT/EP2008/052254, Written Opinion mailed Nov. 10, 2008", 7 pgs.

* cited by examiner

IMPLANT FOR FRACTURE TREATMENT

This application is a U.S. National Phase Patent Application based on International Application Serial No. PCT/EP2008/052254 filed Feb. 25, 2008, the disclosure of which is hereby explicitly incorporated by reference herein.

TECHNICAL FIELD

The invention relates to an implant for fracture treatment of the kind described in claim 1. It furthermore relates to an implant system for fracture treatment.

BACKGROUND

For the treatment of a proximal femur fracture (subtrochanteric or intertrochanteric fracture or femoral neck fracture) with an implant, an intramedullary nail is usually introduced into the femur bone and the femur head is fixed via a femoral neck screw journaled in the proximal section of the medullary nail. The femoral neck screw is guided for this purpose through a slanted bore in the proximal section of the medullary nail and is anchored in the spongiosa of the femoral head by screwing in. In this context, proximal means closer to the body or to the heart of a patient, whereas distal means the opposite.

Femoral neck fractures are furthermore frequently treated in that a plate comprising a sleeve facing in the direction of the femoral neck is fixed laterally to the femur, with the sleeve coming to lie medially in the femur. A femoral neck screw is slidingly guided in the sleeve and its proximal end is anchored in the femoral head.

To achieve a stable anchorage of the femoral neck screw, attempts are in particular made to achieve a stable anchorage of the screw in the femoral head, which also offers security against rotation, by a special embodiment of the thread of the femoral neck screw. It has also already been proposed to introduce both a screw and a pin for security against rotation into the femoral head in parallel. The anchorage of a femoral neck screw, above all in osteoporotic bones, cannot be effected without difficulties.

An osteosynthetic screw also has to be anchored with low stability in bone tissue on other indications for fracture treatment; the proximal humerus could be named by way of example. Furthermore, explanation of the implant after healing has taken place should, where possible, also be possible with implants for fracture treatment, which brings about an additional constraint in comparison with prosthetic applications.

A prosthesis for filling a passage in the femoral head core is known from WO 96/39974. This prosthesis has a porous filling part for the filling of the passage. It is provided to be connected to the bone tissue. Necrotic bone substance is thus reinforced.

A tubular implant is described in US2003/0045885 which can be anchored in the bone in a self-tapping manner, for example. The surface of this implant can be porous to integrate better into the bone tissue. The implant serves for the reinforcement of osteoporotic bone tissue in the area of the femoral neck.

An intramedullary implant for a hip joint prosthesis can be seen from U.S. Pat. No. 3,852,045 which has a firm and structurally loadable central region as well as firmly connected porous regions at each axial end.

SUMMARY

An improved implant for fracture treatment of the initially named kind is set forth in the following which enables an improved anchorage in the bone tissue in addition to further advantageous effects.

This, in addition to a plurality of further advantageous effects, can be achieved by an implant for fracture treatment having the features of claim 1.

This implant is characterized in that it comprises an elongate base body, which is in particular rotationally symmetrical, and an anchorage section, with the anchorage section having an outer surface of a porous material at least in part and with the anchorage section being arranged in an axial end region of the implant and being releasably connected or connectable to the base body. The skilled person unambiguously understands "connectable" to mean that the base body and the anchorage section, for example, are optionally present, for example before the implanting, as separate elements, but can be put together to form the implant in accordance with their purpose by means of a releasable connection and are also configured accordingly. In this context, a releasable connection in particular means that the connection can be separated without any structural damage to one of the connected components; a screw connection could be named here, for example. The base body is an implant shaft, for example. The base body is manufactured, for example, from titanium, stainless steel, a composite material and the like and ensures the structural stability of the implant such that the bone fragments are fixed to one another during the fracture healing, while the fracture point still has a certain loadability before the complete healing of the fracture. The anchorage section has a length, for example, which corresponds to 30% or 25% or less than 20% or even less than 15% of the total longitudinal extent of the implant. A functional separation is so-to-say achieved: the anchorage section serves for the good anchorage in the bone and ensures a large-area distribution of forces which occur as well as an improved anchorage of the base element in the bone, in particular with a poor bone quality such as is particular frequently encountered in the region of the femoral neck, but also in the proximal humerus, for example. The base body is, in contrast, made up of a compact material and ensures structural stability during the healing of the fracture. Since the anchorage section and the base body are releasably connected, the implant can be explanted again after fracture healing has taken place, with only the anchorage sections being fixedly connected to the bone tissue and remaining in the body.

In accordance with an embodiment of the proposed subject matter, the implant can be designed as a femoral neck implant or a femoral neck screw in which the anchorage region is arranged at the proximal end of the implant. The section is understood as the proximal end of the implant here which is implanted in the femoral head, i.e. the section which, in contrast to a distal section, is located closer to the body of a patient. It generally applies here that proximal means closer to the patient's body and distal means oriented toward the extremity. In the case of a femoral neck screw, this also means that the proximal end represents the tip of the screw, whereas the screw head is at the distal end. As already explained above, the use of a porous and in particular biocompatible material in the proximal region of femoral neck implants results in the advantage that a particularly stable anchorage of the implant in the spongiosa of the femoral head can be achieved, which is particularly of great advantage for osteoporotic bones. An outside surface is understood here in the sense of the present disclosure at least as a part region of the total external surface of the proximal end of the femoral neck implant.

It must be stated that all the embodiments of an implant described in the following can also and in particular be used as femoral neck implants, in particular for the treatment of a proximal femoral fracture or of a femoral neck fracture, with then the anchorage section specifically being arranged at a proximal end of the implant, whereas the base body is disposed at distal. Any elements for connection to the anchorage section are then arranged at the proximal end of the base body.

Furthermore, the anchorage section can in each case be designed as a sleeve such that the features of the embodiments described below relating to the anchorage section also respectively cover such a sleeve.

The porous biocompatible material can be a porous carbon substrate that is coated with a biocompatible material in accordance with an embodiment of the proposed implant. In accordance with an embodiment of the proposed implant, the biocompatible material can in particular be tantalum, niobium or an alloy with tantalum and niobium, in particular an alloy of niobium, hafnium and/or tungsten with tantalum or hafnium and/or tungsten with niobium, and the biocompatible material can be applied to the carbon substrate, which is porous to a high degree, by means of a gas phase deposition. A particularly large contact surface of the implant with the bone tissue is thereby provided, whereby the ingrowth of the implant into the spongiosa of the femoral head can be accelerated and the integration of the implant into the spongiosa can be improved. A suitable material is described in detail in U.S. Pat. No. 5,282,861. Such an implant has the advantage with respect to conventional implants such as femoral neck screws made of titanium that the implant results in a better and above all more stable anchorage in bone, for example in the femoral head or in the spongiosa of the femoral head since bone tissue can grow into the pores of the porous material. An especially stable connection of bone tissue and implant is in particular achieved in comparison with conventional implants when the porous biocompatible material can additionally stimulate the bone growth. Above all with osteoporotic bones in which the anchorage of an implant is as a rule critical due to the brittle bone tissue, the proposed implant can nevertheless result in a stable anchorage in a bone such as the femoral head due to the substantially better integration of the implant in the bone. A porous biocompatible material is in particular understood as a material such as is described in U.S. Pat. No. 5,282,861.

A suitable porous material which is particularly suitable for the application described here can be found in the portfolio of the applicant under the name Trabecular Metal™.

In an embodiment of the proposed subject matter, the anchorage section consists completely of the porous material. In this connection, the base body is directly connected to the anchorage section in a releasable manner, for example by screwing a threaded section of the base body into a sleeve made of the porous material.

In another embodiment, the anchorage section includes a substrate at whose outer side the porous material is arranged and is in particular connected to the substrate in a non-releasable manner. In this connection, a non-releasable connection is to be understood as a connection which can essentially not be separated without structural damage. This includes, for example, firmly bonded connections or also adhesively bonded connections or so-called bondings. Embodiments are furthermore to be understood by this in which the porous material was manufactured directly on the substrate such that the component is present in one piece so-to-say. In the further sense, firm pressed connections are also to be understood by this, with the list not intended to be exclusive. The substrate, for example, has means for releasable connection to the base body, with the means being an internal thread in one embodiment and/or an external thread at an axial end of the anchorage section.

An embodiment of the subject matter proposed here is characterized in that the base body is designed as a shaft which is formed with a thread at one end for connection to the anchorage section. In this connection, it can be an external thread for screwing into the anchorage section or also an internal thread. In particular in the case of an external thread, a conical region extends between the shaft and the thread which enlarges in diameter from the thread toward the shaft. The region is provided in an embodiment, on the screwing into an anchorage section, in particular into an anchorage section designed as a sleeve, for the purpose of spreading said anchorage section apart.

In a further embodiment of the subject matter described, the anchorage section has a thread, in particular a spongiosa thread, at an external periphery. In this connection, the implant can be made, for example, in the form of a hybrid femoral neck screw which has a shaft region arranged at distal and a proximal section which is provided with the porous biocompatible material and which includes a spongiosa thread. A distal region of the implant is furthermore in particular designed for the journaling and/or guiding of the implant in an intramedullary nail and/or in a guide sleeve of a hip plate. Such a screw has the advantage that it can be screwed into the femoral head in one workstep, i.e. after a pre-drilling into the femoral head, the hybrid femoral neck screw can be guided directly through a corresponding receiving bore of an intramedullary nail and can be screwed into the prepared bore in the femoral head.

This form of an osteosynthetic screw can naturally also be used analogously for the treatment of other fractures.

Furthermore the anchorage section can be designed as a sleeve. The anchorage section can thereby be easily introduced into the bone, for example, by driving into a bore in the bone using a hammer.

In accordance with a further embodiment, the anchorage section has longitudinal slits or longitudinal grooves in at least an axial region. In this connection, a conical region of the base body described above can be designed to spread the sleeve apart on the screwing into the sleeve. In particular the axial extent of the thread of the base body is in particular smaller than the length of the anchorage section. Due to the spreading apart, the anchorage section is pressed into the spongiosa in the manner of a dowel, which results in an improved anchorage in the bone.

The anchorage section in accordance with a further embodiment has a closed and/or a rounded end section. The closed and/or rounded end in this connection is arranged at the side of the anchorage section remote from the base body. This, for example, facilitates the introduction of the anchorage section or of the implant into a bore.

In accordance with an embodiment, the anchorage section is designed to be smooth at an inner side in the starting state, i.e. in the unused state, such that an external thread of the base body cuts into the interior of the anchorage section on the first screwing in, in particular on the implanting. The anchorage section can thereby, for example, be used with different screw threads and a very stable thread connection results.

A further embodiment of the implant is characterized in that the base body of the implant is designed for the journaling and/or guiding of the implant in a transverse bore of an intramedullary nail and/or of a guide sleeve of a fracture plate.

Furthermore a screw is described, in particular a femoral neck screw, having the features of the embodiments described above and relating to the base body and an anchoring section is described for use in an implant of the kind described above.

A sleeve is further described for use in an implant of the proposed kind, characterized by the features of one of the above embodiments of the implant relating to a sleeve and/or to an anchorage section.

An implant system for fracture treatment is furthermore described comprising a medullary nail with a passage opening for a fixing element and an implant of the kind described above used as a fixing element, with in particular the medullary nail being a proximal femoral nail and the fixing element being a femoral neck implant. Accordingly, an embodiment furthermore relates to an implant system for fracture treatment comprising a medullary nail having a proximal passage opening for a femoral neck implant and a femoral neck implant in accordance with any one of the above embodiments of an implant.

There is likewise described an implant system for fracture treatment comprising a plate for fixing to a bone and a guide sleeve arranged thereon for sliding reception of a fixing means and an implant of the kind described above used as an implant. In accordance with a more specific embodiment, an implant for fracture treatment is furthermore set forth comprising a plate for lateral fixing to the femur and a guide sleeve arranged thereon for the siding reception of a femoral neck implant as well as a femoral neck implant in accordance with any one of the embodiments of an implant described above, with the femoral neck implant in particular having an axial internal thread in a distal region. This is known as a "dynamic hip plate".

Furthermore, a method is set forth for the surgical treatment of a proximal femur fracture or of a femoral neck fracture comprising an implant used as a femoral neck implant as described above, wherein
- an intramedurally nail is introduced into the femur of a patient or a hip plate with guide sleeves is introduced into a patient;
- a bore for the at least part reception of the femoral neck implant is introduced in the spongiosa of the femoral head;
- the femoral neck implant is guided through a slanted bore in the proximal section of the medullary nail or through a guide sleeve of the hip plate and a proximal section of the femoral head implant provided with the porous biocompatible material is screwed into the bore in the femoral head or a sleeve of the femoral head implant provided with the porous biocompatible material is hammered into the bore in the femoral head and a femoral neck screw of the femoral neck implant is guided through a slanted bore in the proximal section of the medullary nail or a guide sleeve of the hip plate and is screwed into the hammered in sleeve. In this connection, in particular a proximal femur fracture is treated with a plate with the help of a nail and a femoral neck fracture with the help of the embodiment with a plate.

It is understood that the aforesaid method can also be transferred analogously to the treatment of other fractures with an implant or an implant system as set forth above.

The features of the aforesaid embodiments of the proposed implant can naturally each be combined with one another to form specific embodiments.

BRIEF DESCRIPTION OF THE DRAWINGS

The invention will be explained in more detail in the following with reference to embodiments shown in the drawings. There are shown in detail FIG. 1 a first embodiment of an implant, for example of a femoral neck implant, in the form of a combination of a screw, for example of a femoral neck screw, and a dowel which can be anchored in the bone.

DETAILED DESCRIPTION

The following description of the embodiments and the drawings serve for the better understanding of the invention and should not be used to restrict the subject matter characterized in the claims. In this connection, the invention will be explained substantially for the example of femoral neck implants, with the transfer easily being possible for the skilled person to implants of the kind described and claimed for the treatment of the fractures such as fractures of the proximal humerus and with the corresponding disclosure being implicitly contained in the embodiments. In this connection, in particular the design of the claimed implant with respect to the essential features contained in the claims is not changed.

Figure 1:
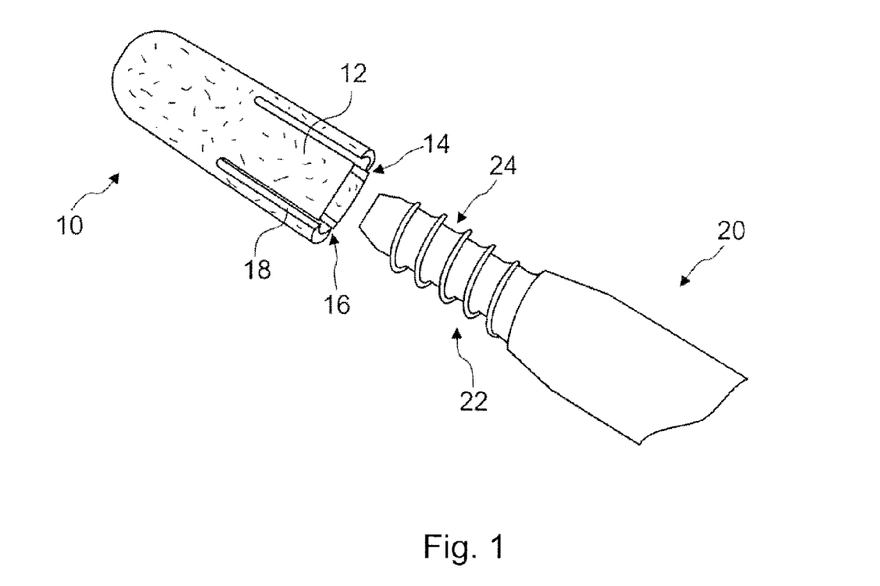

FIG. 1 shows an implant, specifically a femoral neck implant, for example, comprising a femoral neck screw 20 and a dowel 10 which is made from a porous material such as porous tantalum and which is suitable as a bone replacement material and/or as a biocompatible material capable of absorbing cells and tissue. The porous biocompatible material in this connection is similar to the microstructure of the spongiosa of a human bone and facilitates the ingrowth with the spongiosa when it is anchored in the bone. An example of such a material is the biocompatible material marketed by Zimmer as Trabecular Metal™. This material is formed from a glass-like carbon foam substrate with a lattice structure which is coated by means of gas phase deposition (chemical vapor deposition) with a biocompatible material such as tantalum, niobium or an alloy with tantalum and niobium, for example an alloy of niobium, hafnium and/or tungsten with tantalum or hafnium and/or tungsten with niobium. Reference is made in this respect to U.S. Pat. No. 5,282,861 which describes suitable biocompatible materials for the proposed subject matter and their manufacture and whose content is herewith included in this application. What is important is that the biocompatible material used is suitable to act as a prosthesis for bone tissue and to stimulate the growth of bone tissue when it is positioned directly in the bone tissue, i.e. in the spongiosa. In this connection, in particular the pores of the biocompatible material act as a matrix for the absorbing and anchorage of bone tissue, in particular spongiosa tissue, and thus promote a particularly good ingrowth of an implant manufactured from such a biocompatible material with the spongiosa.

Figure 2:
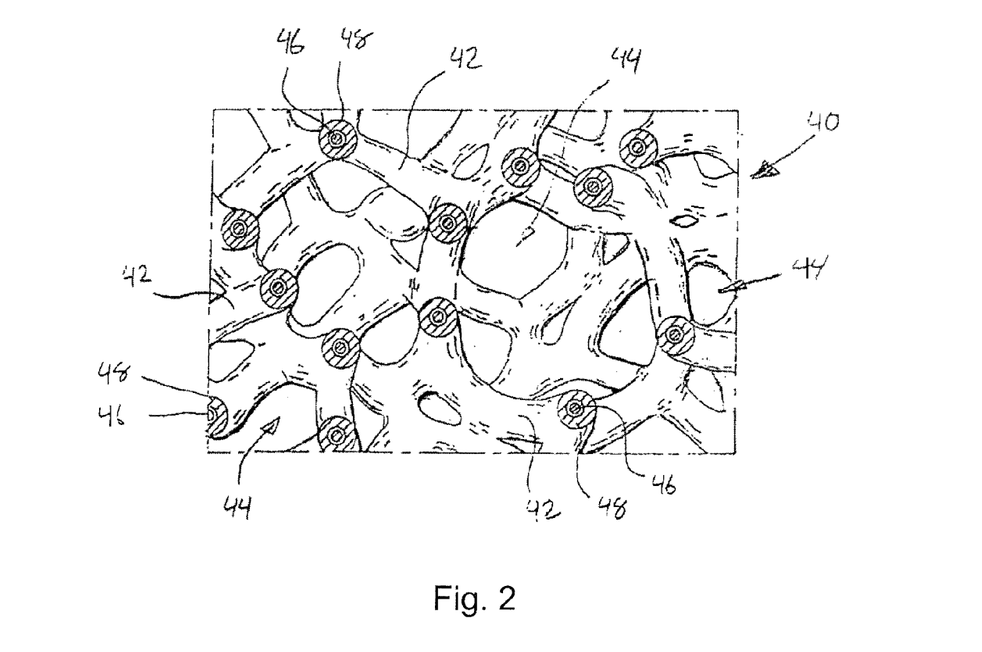
FIG. 2 in a greatly magnified view, a section of the material, which is porous to a high degree, for example of tantalum, which is used in accordance with this disclosure.
Figure 3A:
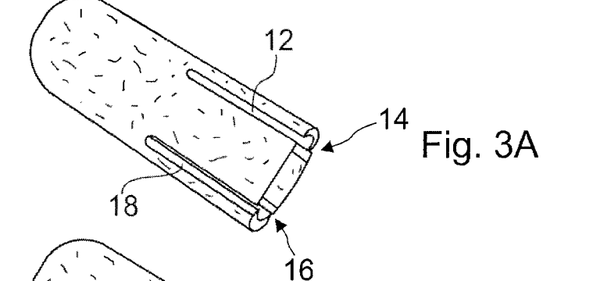
FIGS. 3A-3D various embodiments of the dowel of the first embodiment of an implant, in particular of a femoral neck implant.
Figures 3B, 3C, 3D:
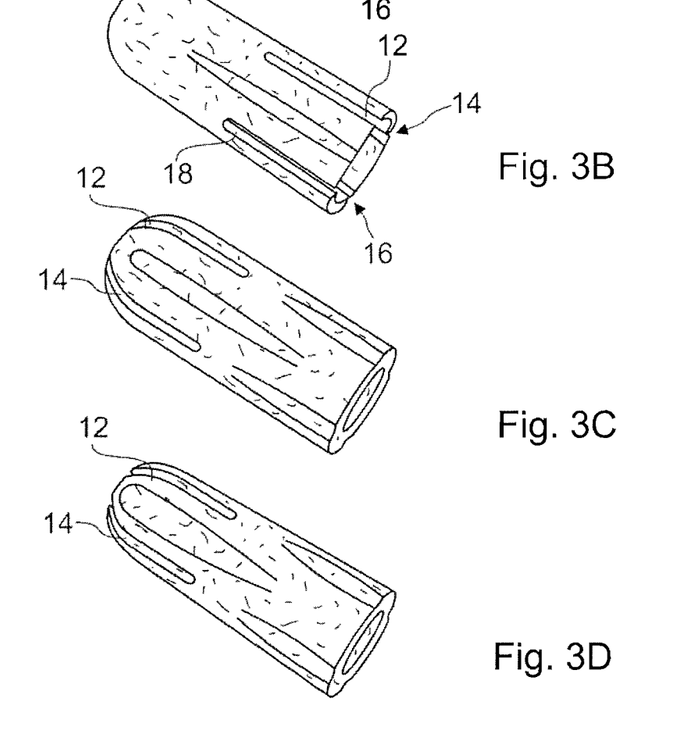

FIG. 2 shows a porous tantalum structure 40 such as is particularly well suited as a biocompatible porous material. The structure 40 has a large number of webs 42 which define the open spaces 44 therebetween. Each web 42 generally has a carbon core 46 which is covered by a thin film of metal 48 such as tantalum. The open spaces 44 between the webs 42 form a matrix of thoroughgoing passages which substantially do not have any dead ends so that the growth of bone tissue is not impeded by the porous tantalum structure. The structure has a large similarity with the geometry of bone trabeculae and thus further promotes the ingrowth of bone tissue. The porous tantalum can have up to approximately 75% to approximately 85% or more empty space therein. This porous tantalum structure is therefore a lightweight, but nevertheless rigid porous structure, i.e. a structure loadable with high forces, which is substantially uniform and consistent in its composition and is very similar to the structure of natural bone tissue. A matrix is thereby provided into which natural bone tissue can grow and can properly anchor an implant consisting thereof in the surrounding bone tissue of a patient. The porous tantalum structure 40 can be manufactured with different densities to be adapted ideally to the bone tissue into which the implant is integrated; in this respect, see also the already mentioned U.S. Pat. No. 5,282,861.

Figure 4:
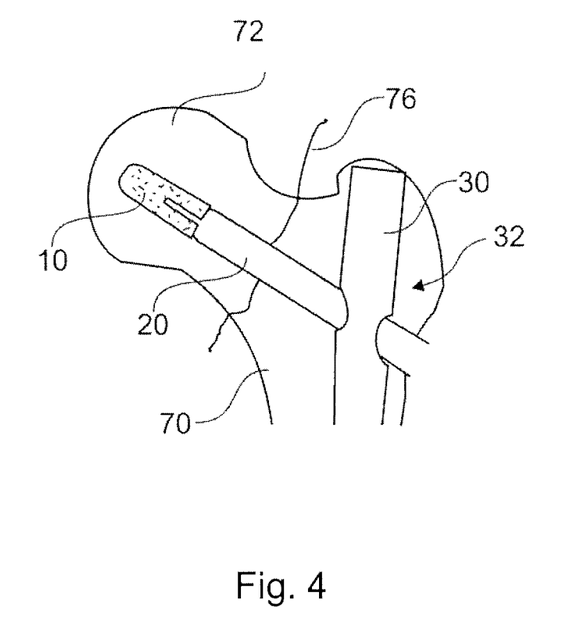
FIG. 4 a proximal femur fracture treated with a femoral neck implant in accordance with the first embodiment.

The dowel 10 of the femoral neck implant shown in FIG. 1 has four longitudinal slits 12, 14, 16 and 18 which give the dowel 10 a specific elasticity, which facilitates the screwing in of the femoral neck screw 20 and also enables a spreading apart to a specific degree of the dowel 10 with a screwed in femoral neck screw 20. The femoral neck screw 20 has a threaded section 24 at its end 22 with which the screw 20 is screwed into the dowel 10 as well as a conical or conically formed region which adjoins at distal and which is designed such that it can spread apart the dowel 10. FIGS. 3A to 3D show different embodiments of the dowel 10: in the embodiments shown in FIGS. 3A and 3B, longitudinal slits are provided in the distal section of the dowel 10, or in more general terms in the section of the dowel 10 oriented toward the base body or the screw, whereas the embodiments shown in FIGS. 3C and 3D have longitudinal slits for spreading apart in the proximal or "tip-side" section of the dowel 10. Surgically, the dowel 10 is first introduced into a corresponding bore in the femoral head; subsequently, the femoral neck screw 20 is screwed into the dowel 10 introduced in the femoral head. Alternatively, the femoral neck implant comprising the dowel 10 and the screw 20 can also already be preinstalled, i.e. the screw 20 can already be screwed so far into the dowel 10 that the dowel 10 is not yet spread apart and can therefore easily be introduced into the bore in the femoral head. The implant is then hammered in, for example. FIG. 4 shows a proximal femur fracture 76 treated with a femoral neck implant described above. An intramedullary nail 30 is introduced into the femur 70. A slanted bore is provided in the proximal section 32 of the medullary nail 30 through which the femoral neck screw 20 is guided and which it is journaled. The femoral neck screw 20 is screwed into the dowel 10 introduced into the femoral head 72, whereby the dowel 10 is spread apart somewhat in the femoral head.

Figure 5:
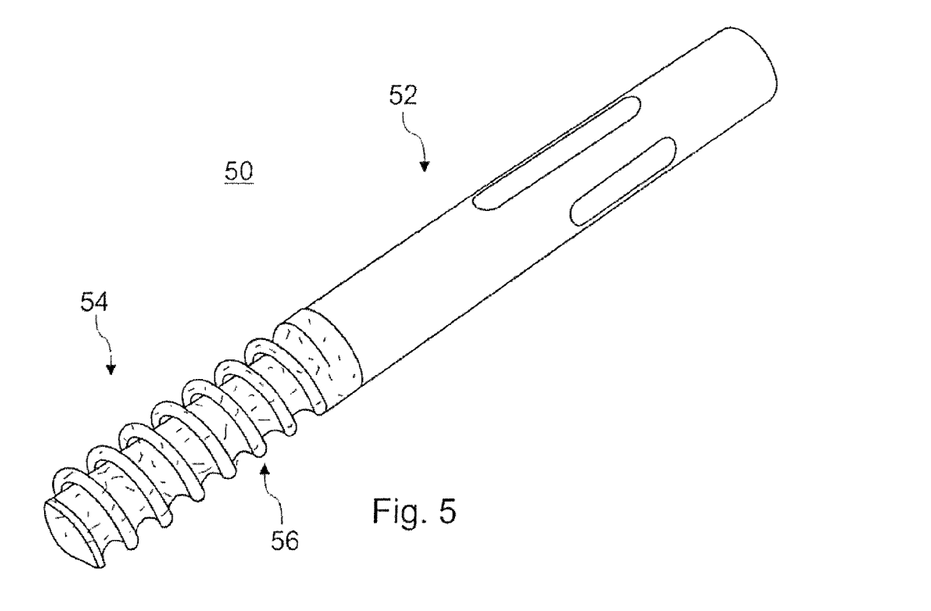
FIG. 5 a second embodiment of a femoral neck implant proposed here in the form of a hybrid femoral neck screw.
Figure 6:
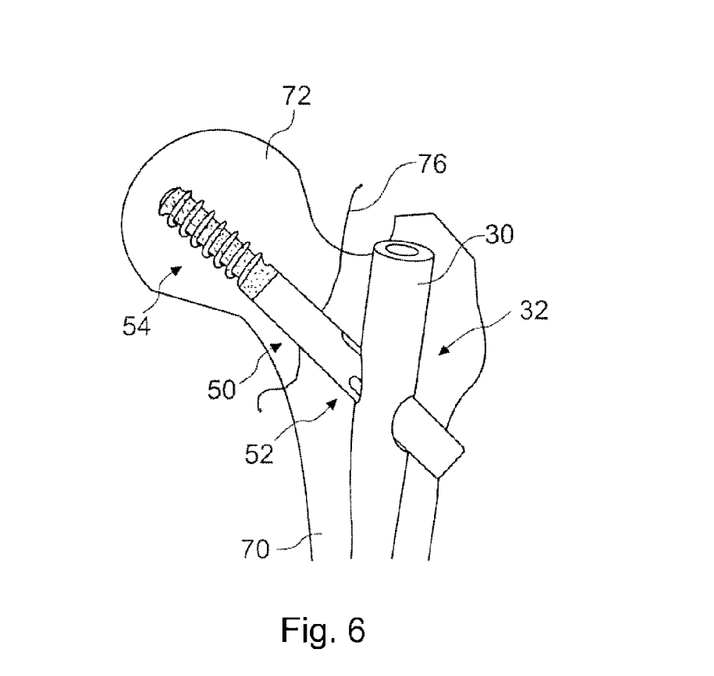
FIG. 6 a proximal femur fracture treated with a femoral neck implant in accordance with the second embodiment.

FIG. 5 shows, as a further embodiment, a hybrid femoral neck screw 50 having a distal section 52 which serves for the journaling of the screw 50 in a slanted bore of an intramedullary nail and having a proximal section 54 which is made from a porous material and has a spongiosa thread 56 for screwing into the spongiosa of the femoral head. The ingrowth of bone tissue into the proximal section 54 is promoted due to the porosity of the proximal section 54, which effects a particularly good anchorage of the femoral neck screw 50 in the femoral head. FIG. 6 shows the anchorage and position of the femoral neck screw 50 in the femur 70 and femoral head 72.

Figure 7:
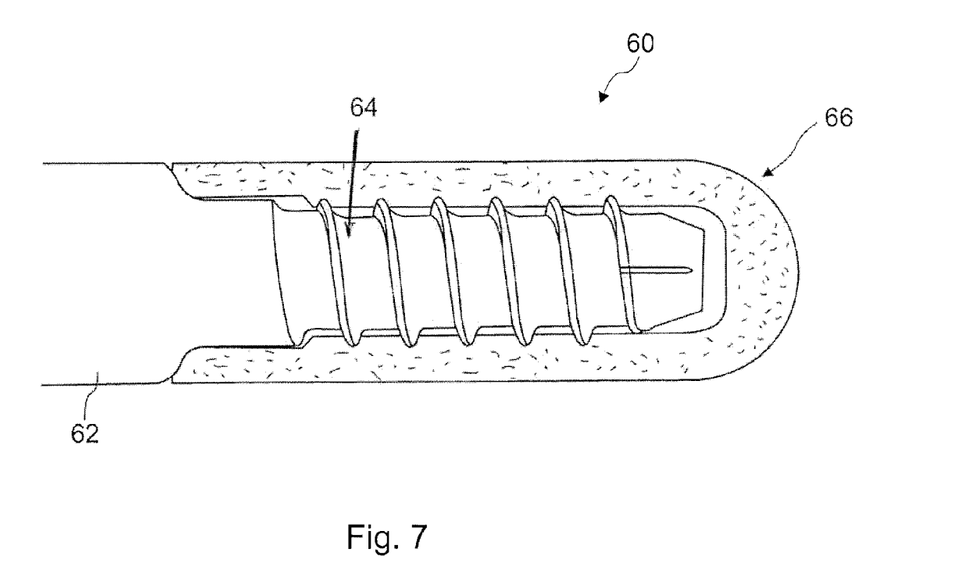
FIG. 7 a femoral neck implant in the form of a combination of a femoral neck screw and of a sleeve which can be hammered into and anchored in the femoral head and into which a femoral neck screw can be screwed.

FIG. 7 shows by way of example a possible connection of a base body 62 in a section having an anchorage section designed as a sleeve or dowel and made from porous material by means of an external thread 64 on an end of the base body, that is, for example, on the proximal end of a femoral neck screw. The anchorage section has a rounded and closed end 66.

It must be stated that, depending on the embodiment and the implanting technique, only the base body, or also the total implant together with the anchorage section, can be cannulated to enable a guided implanting via a guide wire.

Figure 8:
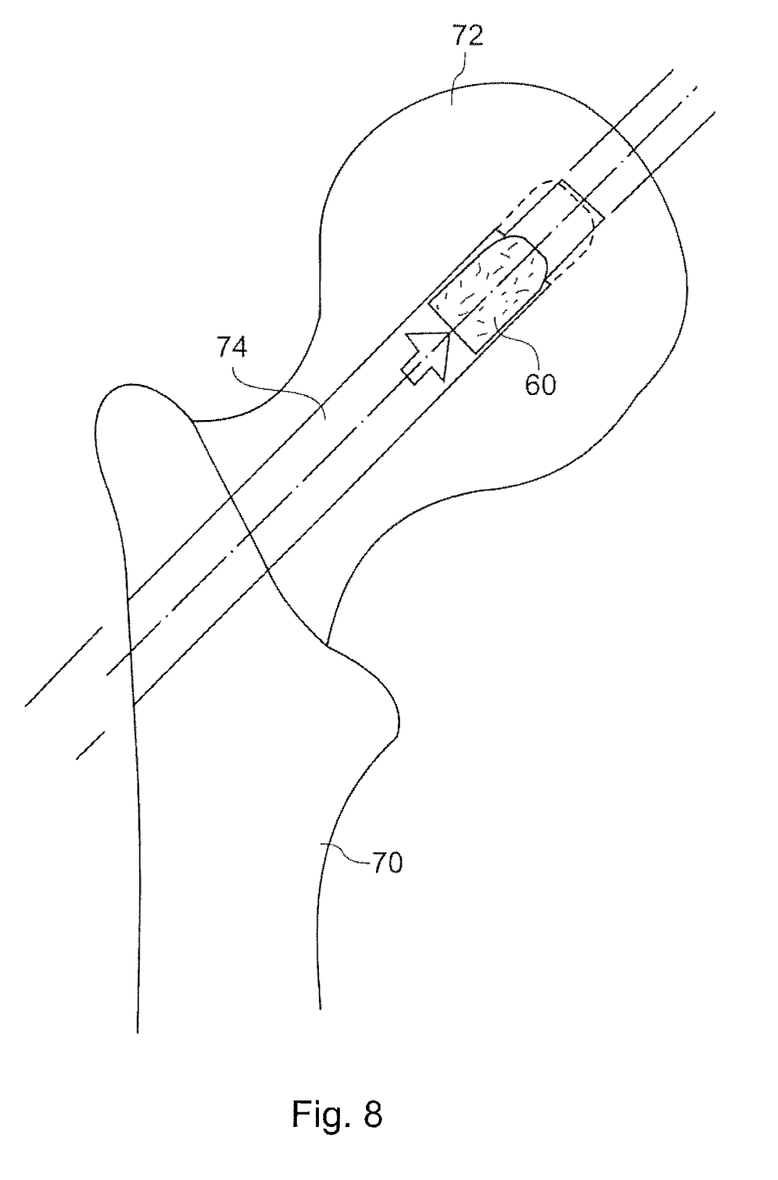
FIG. 8 the introduction of a femoral neck implant into the femoral head for the treatment of a proximal femur fracture.

FIG. 8 shows a possibility for how the sleeve 60 shown in FIG. 6 can be introduced into the femoral head: First, a bore 74 is produced in the spongiosa of the femoral head 72 by means of a stepped reamer or by means of a stepped broach, for example, for the reception of the sleeve 60 and of the femoral neck screw 62. The sleeve 60 is then hammered into the bore until it is seated firmly in the bore at a desired depth in the femoral head 72. Subsequently, the femoral neck screw 62 is screwed into the sleeve 60. Alternatively, the screw 62 already screwed into the sleeve 60 can also be hammered into the femoral head 72 as the preassembled combination of sleeve 60 and screw 62.

Figure 9:
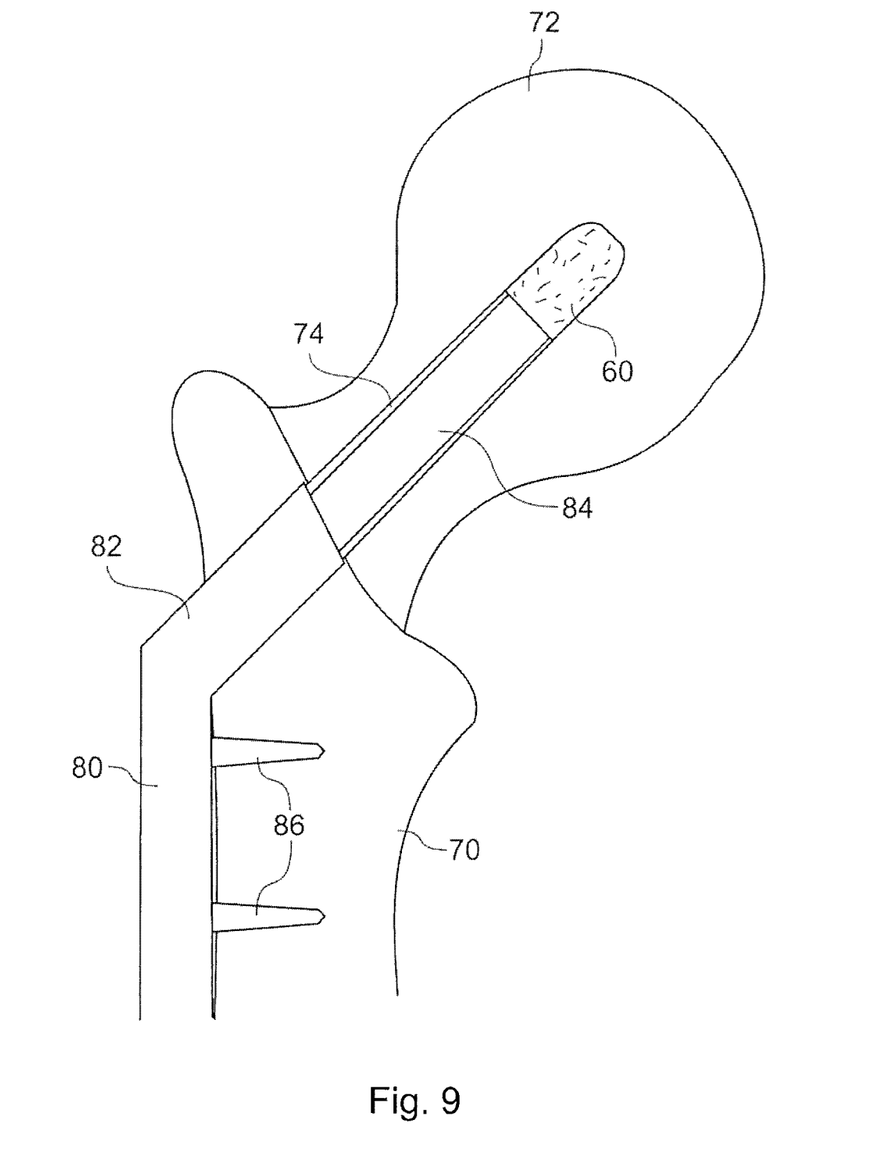
FIG. 9 an implant for treatment of a femoral neck fracture comprising a plate for the lateral fixing to the femur and a guide sleeve for the sliding reception of a femoral neck implant.

FIG. 9 shows the treatment of a femoral neck fracture of the femur 70 with an implant comprising a plate 80 for the lateral fixing to the femur 70 by means of corticalis screws 86. The plate 80 has a guide sleeve 82 for the sliding reception of a femoral neck implant. The guide sleeve 82 is introduced into a bore in the femur 70. The femoral neck implant slidingly journaled in the guide sleeve 82 includes a screw 84 which is screwed into a sleeve 60 anchored in the femoral head 72 and made from porous tantalum at its proximal end provided with a thread. The screw 84 is thereby fixed to the proximal end, whereas it is slidingly journaled in the guide sleeve 82 at its distal end. The screw 84 has at its distal region which is located in the guide sleeve 82 an axial internal thread into which a compression screw (not shown) is screwed in the assembled state of the implant. The compression screw serves above all to limit the sliding movement of the screw 84 in the guide sleeve 82 and to exert at least a specific compression effect on the fracture. The advantage of such an implant above all consists of as good as no longitudinal forces being transmitted by the slidingly journaled screw 84 onto the femur 70 and femoral head 72 and thus of the compression effect which occurs being able to be limited. A plate 80 with a guide sleeve 82 is in another respect offered for sale by the applicant as the Dynamic Hip Screw DHS.

In the following it is described how the femoral neck implants described above can be surgically implanted. An implant can be introduced into the body of a patient in an open manner, i.e. by means of presenting the proximal femur fracture, or in a minimally invasive manner using a special target device (not shown). An intramedullary nail 30 is first introduced into the femur 70 of a patient. This can be done using the mentioned target device. A bore 74 is then introduced into the spongiosa of the femoral head 72 for the reception of the femoral neck implant 10, 50 or 60. When the femoral neck screw 50 is used as the femoral neck implant, the screw 50 is then guided through a slanted bore in the proximal section 32 of the medullary nail 30 and its proximal section made from the porous biocompatible material is screwed into the bore 74 in the femoral head 72. When a combination of dowel 10 or sleeve 60 and of femoral neck screw 20 or 62 is used, the dowel 10 or the sleeve 60 can first be hammered into the bore 74 in the femoral head 72 and subsequently the femoral neck screw 20 or 62 can be guided through a slanted bore in the proximal section 32 of the medullary nail 30 and can be screwed into the hammered in dowel 10 or the hammered in sleeve 60. Alternatively, the already preassembled combination of dowel 10 or sleeve 60 and of femoral neck screw 20 or 62 can also be hammered into the bore 74 in the femoral head 72 and subsequently the femoral neck screw 20 or 62 can be completely screwed into the dowel 10 or the sleeve 60.

Figure 12:
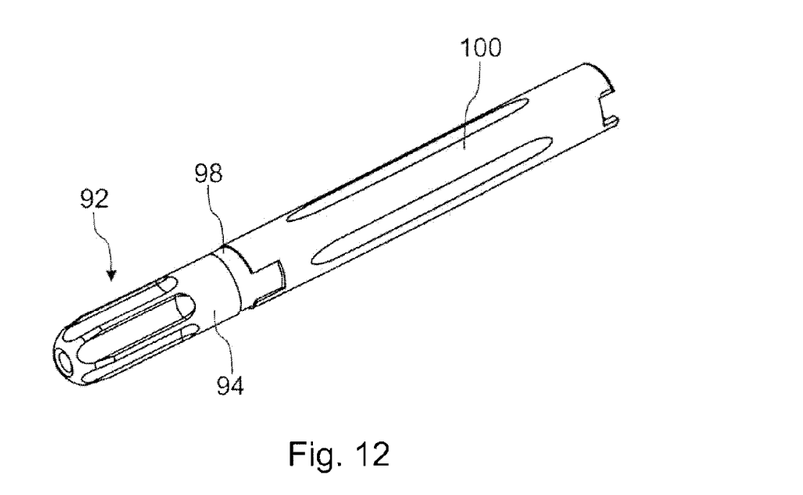
FIG. 12 a perspective representation of the multipart femoral neck implant in accordance with FIGS. 10 and 11.

FIG. 12 shows a further embodiment of an implant of the kind set forth in the form of an implant, for example of a femoral neck implant 90 here, that is anchored at its one end in the femoral head and is journaled at its other end in an intramedullary nail. The implant 90 shown includes an anchoring section 92 and an elongate base body 96 which comprises a shaft 100. The shaft 100 is formed, for example, from titanium steel for reception in a slanted bore of the intramedullary nail. The fastening section includes a substrate 98 and a jacket 94 made from porous biocompatible material so that the implant can be anchored ideally in the femoral head at the end anchored in the femoral head. The substrate has an internal thread 99. Both the parts 96 and 92 are connected to one another by means of a screw 102 which is screwed into the internal thread 99. The whole implant is cannulated. The screw 102 is released and removed from the implant for the removal of the shaft 100. The base body 96 can accordingly be removed from the body of a patient, with the anchorage section 92 of the implant remaining in the femoral head since the bone tissue is ingrown with the porous biocompatible material.

Figure 10:
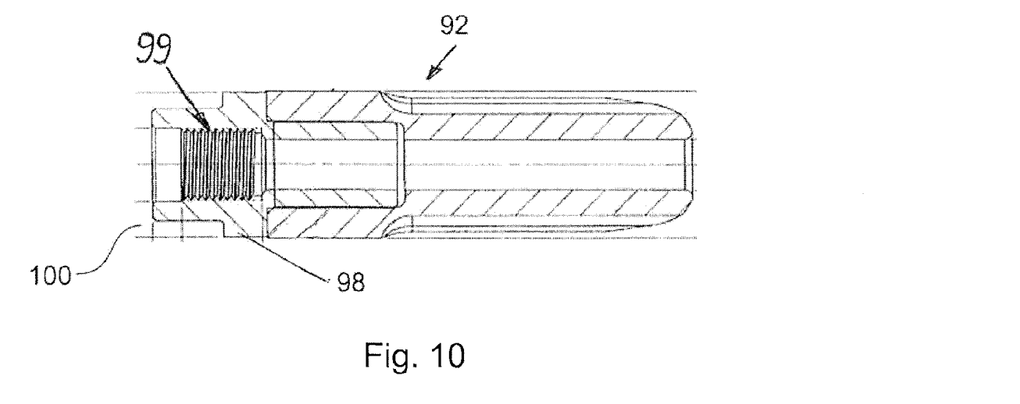
FIG. 10 a cross-section through the anchorage section of a femoral neck implant in accordance with a further embodiment.
Figure 11:
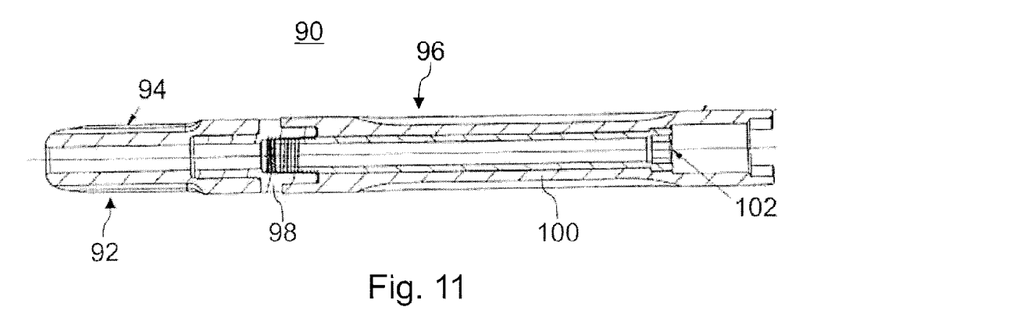
FIG. 11 a cross-section through the femoral neck implant of FIG. 10 in the assembled state.

FIG. 12 shows a perspective view of the implant from FIGS. 10 and 11. It can be recognized that the anchorage section is provided with longitudinal grooves.

Although the invention has been explained in the above embodiments with reference to specific embodiments and in particular to femoral neck implants, this should not represent any limitation for the claimed invention. The application of the invention to other indications and the corresponding implants are also directly revealed to the skilled person with reference to the total disclosure of the present application and of the exemplary embodiments.

The reference numerals used designate the following elements shown in the drawing:

- 10 dowel of porous tantalum
- 12 longitudinal slit of the dowel
- 14 longitudinal slit of the dowel
- 16 longitudinal slit of the dowel
- 18 longitudinal slit of the dowel
- 20 base body, femoral neck screw
- 22 proximal end section of the femoral neck screw
- 24 threaded section of the femoral neck screw
- 30 intramedullary nail
- 32 proximal section of the intramedullary nail
- 40 porous tantalum structure
- 42 webs of the porous tantalum structure
- 44 open spaces between the webs
- 46 carbon core of a web
- 48 metal layer
- 50 hybrid femoral neck screw
- 52 distal section of the hybrid femoral neck screw
- 54 proximal section of porous tantalum
- 56 spongiosa thread
- 60 sleeve or dowel
- 62 femoral neck screw
- 64 thread of the femoral neck screw
- 66 end section of the sleeve or of the dowel
- 70 femur
- 72 femoral head
- 74 bore in the femoral head
- 76 proximal femur fracture
- 80 plate for the lateral fixing to the femur
- 82 guide sleeve for a femoral neck implant
- 84 femoral neck screw
- 86 corticalis screw
- 90 multipart femoral neck implant
- 92 anchoring section
- 94 outer side of porous material
- 96 base body
- 98 substrate of the anchorage section
- 99 internal thread
- 100 shaft
- 102 screw

The invention claimed is:

1. An implant for fracture treatment, the implant comprising:
   an elongate base body having an axial end region;
   a screw extending through a portion of the elongate base body and including an external threaded section at or near the axial end region;
   an anchoring section having an outer surface at least partially comprising a porous material; and
   a substrate non-releasably coupled to the anchoring section, the substrate having a first end, at least partially surrounded by the anchoring section, and a second end, at least partially surrounded by the elongate base body, the second end including an internal threaded section configured to engage the external threaded section of the screw,
   wherein a portion of the internal threaded section is surrounded by the elongate base body, and
   wherein the substrate and the anchoring section are removably coupled, as an integral unit, to the axial end region of the elongate base body and the screw.

2. The implant of claim 1, wherein the implant is a femoral neck implant having a distal end and a proximal end, the anchoring section forming the proximal end of the implant.

3. The implant of claim 1, wherein the anchoring section consists completely of the porous material.

4. The implant of claim 1, wherein the substrate includes an outer surface fixedly coupled to the porous material of the anchoring section.

5. The implant of claim 1, wherein the elongate base body is cannulated to receive the screw.

6. The implant of claim 1, wherein the anchoring section includes a sleeve.

7. The implant of claim 1, wherein the anchoring section includes at least one of a plurality of longitudinal slits or a plurality of longitudinal grooves to expand the diameter of the anchoring section when coupled to the substrate.

8. The implant of claim 1, wherein the anchoring section includes an inner channel that is coupled to the first end of the substrate.

9. The implant of claim 1, further comprising an intramedullary nail having a transverse bore sized to receive the elongate base body, the elongate base body extending through the transverse bore and toward a femoral head.

10. An implant for fracture treatment, the implant comprising:
   an elongate base body having an axial end region;
   a screw extending through a portion of the elongate base body and including a threaded section at or near the axial end region;
   an anchoring section having an outer surface at least partially comprising a porous material; and
   a substrate non-releasably coupled to the anchoring section, the substrate having a first end, at least partially surrounded by the anchoring section, and a second end, at least partially surrounded by the elongate base body, the second end including a threaded section configured to engage the threaded section of the screw,
   wherein the threaded section of the second end engages with the threaded section of a screw outside a portion surrounded by the anchoring section, and
   wherein the substrate and the anchoring section are removably coupled, as an integral unit, to the axial end region of the elongate base body and the screw.

11. The implant of claim 1, where in the threaded section of the screw is engaged with and in direct contact with the second end of the substrate but is not in direct contact with the anchoring section.

\* \* \* \* \*

UNITED STATES PATENT AND TRADEMARK OFFICE
CERTIFICATE OF CORRECTION

PATENT NO. : 9,023,046 B2  
APPLICATION NO. : 12/531557  
DATED : May 5, 2015  
INVENTOR(S) : Keller et al.

Page 1 of 1

It is certified that error appears in the above-identified patent and that said Letters Patent is hereby corrected as shown below:

On the title page, item (75), in "Inventors", in column 1, line 7, delete "Randolph," and insert --Rockaway Township,--, therefor Signed and Sealed this  
Thirteenth Day of October, 2015

Michelle K. Lee  
*Director of the United States Patent and Trademark Office*